United States Patent [19]

Burkhart et al.

[11] Patent Number: 5,674,536
[45] Date of Patent: Oct. 7, 1997

[54] FUNGICIDE COMPOSITIONS

[76] Inventors: Alexander Burkhart; Mario Burkhart, both of Guldengasse 11, Sasbach 79361, Germany

[21] Appl. No.: 256,264

[22] PCT Filed: Dec. 23, 1992

[86] PCT No.: PCT/EP92/02988

§ 371 Date: Jun. 24, 1994

§ 102(e) Date: Jun. 24, 1994

[87] PCT Pub. No.: WO93/12658

PCT Pub. Date: Jul. 8, 1993

[30] Foreign Application Priority Data

Dec. 24, 1991 [DE] Germany .............. 41 42 974.5

[51] Int. Cl.[6] .............................................. A01N 43/38
[52] U.S. Cl. ........................................................ 424/601
[58] Field of Search ................................................ 424/601

[56] References Cited

U.S. PATENT DOCUMENTS

| | | |
|---|---|---|
| 4,075,324 | 2/1978 | Thizy et al. . |
| 4,119,724 | 10/1978 | Thizy et al. . |
| 4,139,616 | 2/1979 | Ducret et al. . |
| 4,849,219 | 7/1989 | Staub et al. . |

FOREIGN PATENT DOCUMENTS

| | | |
|---|---|---|
| A 0 139 374 | 5/1985 | European Pat. Off. . |
| A 0 230 209 | 7/1987 | European Pat. Off. . |
| A 2 187 222 | 1/1974 | France . |
| 392 947 | 3/1985 | France . |
| AS 10 60 660 | 7/1959 | Germany . |
| A 2 328 310 | 12/1973 | Germany . |
| A 2 453 401 | 5/1975 | Germany . |
| A 2 927 994 | 1/1980 | Germany . |
| A 3 125 422 | 1/1983 | Germany . |
| A 3 344 433 | 6/1984 | Germany . |
| A 3 309 765 | 9/1984 | Germany . |
| A 3 410 011 | 10/1984 | Germany . |
| PS 476 293 | 4/1989 | Germany . |
| A 3 039 875 | 6/1991 | Germany . |
| 303 949 | 3/1955 | Switzerland . |
| A 2 238 960 | 6/1991 | United Kingdom . |

OTHER PUBLICATIONS

Database WPIL, An 91-219264 and JP-A 3141206 see abstract Oct. 1989.

Database WPIL An 85-226607 and Jp-A 60 146 808 see abstract D.E.H. Frear "Chemistry of Insecticides, Fungicides and Herbicides" Aug. 1985.

*Primary Examiner*—Brian M. Burn
*Attorney, Agent, or Firm*—Bardehle, Pagenberg, Dost, Altenburg, Frohwitter, Geissler & Partners

[57] ABSTRACT

Fungicide composition comprising a combination of active substances for prophylactic and acute treatment of fungus diseases in plants, whereby one active substance is a phosphite characterized in that the composition includes at least one phosphite selected from the group $K_2HPO_3$, $K_2PO_3$, $Na_2HPO_3$ and $NaH_2PO_3$, lecithin, and at least one of the two compounds selected from sodium metasilicate and soda waterglass.

12 Claims, 1 Drawing Sheet

FUNGICIDE COMPOSITIONS

FIELD OF THE INVENTION

The invention relates to fungicide compositions having a combination of active substances based on phosphites for the prophylactic and acute treatment of fungus diseases of plants, in particular in vineyards and in the cultivation of fruit, arable land, vegetables and hops and of ornamental plants.

BACKGROUND OF THE INVENTION

For the control of fungus diseases in plants it is known to use derivatives of phosphorous acid as well as conservative toxic active substances such as copper, which accumulates in the ground and sulphur. These refer to anorganic and organic salts, of which the latter are available in the form of alkyl compounds or esters of phosphorous acid. A disadvantage of organic phosphite compounds is that these can also be injurous usually to human beings, animals, plants and micro-organisms and can pollute the environment to a serious degree. For prophylactic protection of plants such as roses, ornamental plants or cucumbers against powdery mildew (oidium), a preparation with the active substance lecithin is available commercially. For prophylactic treatment of fungus diseases in fruit orchards and vineyards, the active substance soda waterglass is commercially available. Disadvantages of the above-mentioned active substances are that they are only prophylactically effective in a limited application range. In addition, a disadvantage of waterglass is that it is only sufficiently prophylactically effective in a relatively high concentration and must be applied with care because of its high basicity.

Accordingly, spraying may not be carried out during sunshine, otherwise burning may occur. Further, the waiting period is three weeks.

SUMMARY OF THE INVENTION

It has now been found that a surprisingly high synergistic fungicide effect can be achieved through a combination of an anorganic phosphite with further active substances as defined in claim 1.

The subject matter of the present invention is therefore a fungicide composition made from several active substances whereby one active substance is a phosphite characterized in that the composition includes a combination of active substances from at least one phosphite selected from the group $K_2HPO_3$, $KH_2PO_3$, $Na_2HPO_3$ and $NaH_2PO_3$, lecithin and at least one compound selected from sodium metasilicate and soda waterglass.

A further subject matter of the invention is a method of applying the above-mentioned fungicide compositions.

DETAILED DESCRIPTION OF THE INVENTION

Figure 1:
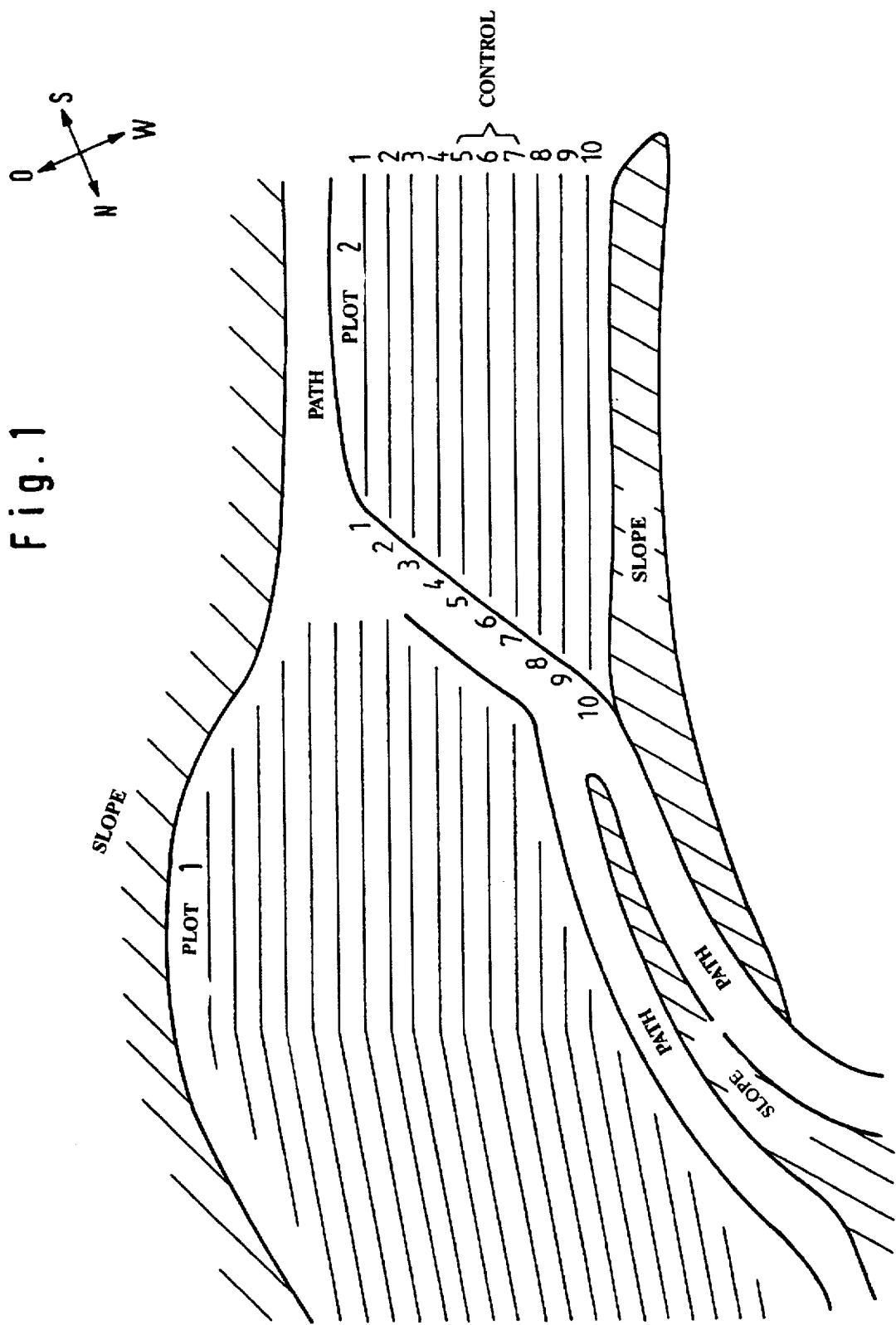
FIG. 1 is a top view of test plots.

As is shown by the embodiments, the compositions in accordance with the invention produce their effect not only prophylactically against fungus attack/infestation, but also by acute fungus infestation, in particular against peronospora and powdery mildew (oidium).

As well as the high effectivity compared with previously known fungicides, the compositions in accordance with the invention demonstrate an excellent environmental compatibility with respect to human beings, animals, plants and micro-organisms.

Methods of manufacturing potassium and sodium phosphites for control of fungus diseases are state of the art and are known to persons skilled in this art.

In a preferred embodiment of the invention the potassium and/or sodium phosphite is used in the composition in the form of a solution. This phosphite solution is preferably manufactured in such a way by mixing phosphorous acid with solid potassium or sodium hydroxide or potassium or sodium hydroxide solution so that a pH value of 5 to 7, preferably about 6 is achieved. This solution, the so-called spraying preparation, serves as the initial solution for the manufacture of a spraying liquor. For this purpose, the above-mentioned solution is preferably diluted with water in the proportion of about 1 to 100. This spraying liquor has preferably a concentration of 0.05–0.1% by weight of phosphite, in particular 0.07–0.09% by weight and 0.075–0.08% by weight is particularly preferred, whereby these values relate to a watery composition applied until the plants are dripping wet, in particular in vineyards and fruit orchards, on arable land and in vegetable gardens as well as in hop farming and with ornamental plants. A prophylactic and acute effect can be determined against peronospora therewith.

The spraying liquor containing phosphite is mixed in a preferred embodiment of the invention with lecithin, preferably in a concentration of 0.04–0.8% by weight and particularly preferred is 0.05% by weight in relation to a watery composition. A suitable commercially available preparation for lecithin is "Neudorffs Bio Blatt" from the company Neudorff, which is effective against powdery mildew on cucumbers, roses and ornamental plants in accordance with the manufacturer's literature and which contains the active substance 25% lecithin from soyabean plants.

In a preferred embodiment of the invention, the above-mentioned spraying liquor containing phosphites is additionally mixed with sodium metasilicate and/or soda waterglass, preferably in a concentration of 0.1–0.5% by weight, whereby 0.2–0.3% by weight is particularly preferred with relation to a watery composition. In a further preferred embodiment of the invention at least a part of the phosphorous acid is mixed directly with soda waterglass and/or sodium metasilicate and if desired without addition of additional potassium sodium hydroxide or solutions thereof. Suitable commercially available products for sodium metasilicate and soda waterglass are products marketed by the company Brenntag AG which contain $Na_2SiO_3$ or $Na_2O$ and $SiO_2$.

Depending upon the application, the active substances lecithin and sodium metasilicate and/or soda waterglass can be mixed individually to the phosphite containing spraying liquor.

In addition to the above-mentioned components, the compositions in accordance with the invention, can additionally and preferably be mixed with watery extracts and solutions of compost and/or worm humus in a concentration of about 50–100 g/100 l of a watery composition and/or potassium hydrogen tartrate (tartar) in a concentration of 2–50 g/100 l of a watery composition as these have a positive effect upon the activation of stability of the metabolism and demonstrate an improved immunological reaction in the plants.

The application of the composition in accordance with the invention is preferably carried out by spraying with treatment of the leaves and/or treatment of the ground, whereby the quantity applied is between 500 (e.g. in the trifoliolate stage) and 2500 l (e.g. with adult plants) of spraying liquor per hectare of area according to plant growth. In the spraying procedure the wetting is performed to dripping wetness. In a less preferred embodiment of the invention the application is carried out by a sprinkling method.

The compositions in accordance with the invention are storable in the absence of soda waterglass and in the absence of air for up to about three years without the effectivity being altered appreciably. When using of soda waterglass, this should be added to the composition in accordance with the invention preferably shortly before use. In accordance with the invention, all active components can also be added immediately before use.

The following embodiments describe the invention. The tests which are described were all carried out in open country on vineyards (see FIG. 1 and the explanation below).

I. Manufacture and application of the potassium phosphite solution 1.574 l phosphorous acid (50%, Riedel de Haen AG) is made up to 5 l with water (solution no. 1) and in the same manner 1.07 kg potassium hydroxide flakes are made up to 5 l with water (solution no. 2).

Solutions no. 1 and 2 are mixed together whereby a pH value of about 6 is achieved.

For the manufacture of the initial products for the spraying liquor, the above-mentioned solution, the so-called spraying preparation, is diluted with water in the ratio of 1:100. The application is made by wetting to dripping wetness.

Generally a prophylactic and acute effect against peronospora could be determined therewith.

II. Manufacture and application of the spraying liquor

1. Spraying liquor with phosphite and lecithin 0.17 l of 25% lecithin solution ("Neudorff's Bio Blatt", of W. Neudorff GmbH KG, Emmerthal) is added to 100 l of the above-mentioned phosphite-containing spraying liquor. The application is carried out by wetting to dripping wetness.

With spraying tests carried out with this spraying liquor an improved prophylactic effect with practically 100% success against peronospora and powdery mildew (oidium) could be determined in comparison with the individual active substances.

2. Spraying liquor with phosphite and soda waterglass 0.6 l soda waterglass (components: 8.1% $Na_2O$, 27.2% $SiO_2$, 64.6% $H_2O$ and 35.3% turbidity matter; Messrs. Brenntag AG, Mehlheim/Ruhr) is added to 100 l phosphite-containing spraying liquor (from example I.). The application was carried out in a similar manner to the previous example.

This spraying liquor was sprayed onto the vineyard on hilly slopes schematically shown in FIG. 1 with cultivated gapes of the Sylvaner variety (for the results see tables 1 and 2). As can be derived from FIG. 1, the vineyard was divided into two test plots, from which plot 2 was further divided into 10 rows, with rows 5–7 as control rows which were not treated with fungicide. The sprayings occurred on the respective dates as given, i.e. a total of six times (spraying nos. 1–6). The plots were examined about one day after the spraying day, i.e. the percentage values given relate to the fungus infestation values after a period of one day after the spraying. By using the composition in accordance with the invention (see example II.3. below) the effect occurred already overnight and no changes could be determined during the further observation periods. On the other hand in all the other cases, in which the composition in accordance with the invention was not used, an increase in the fungus infestation could be observed after about one week (see the comments in the tables thereto).

3. Spraying liquor with phosphite, lecithin and soda waterglass 0.17 l lecithin solution (similar to II.1.) and 0.6 l soda waterglass (similar to II.2) were mixed with 100 l phosphite-containing spraying liquor (from example I.). The application was carried out in a similar manner to the previous examples.

TABLE 1

PLOT 1
VARIETY: SYLVANER
POSITION: SLOPE

| DATE | SPRAY No. | TREATMENT WITH PHOS. | WATGLS. | LEC. | INFESTATION WITH MILDEW LEAF | SHOOTS | GRAPE | INFESTATION with Peronospora LEAF | SHOOTS | GRAPE | OBSERVATIONS |
|---|---|---|---|---|---|---|---|---|---|---|---|
| 13.6.91 | 1 | X | X | — | 1% | 1% | 0 | 0 | 0 | 0 | Light infestation |
| 28.6.91 | 2 | X | X | — | 2% | 2% | 0 | 0 | 0 | 0 | Light infestation |
| 2.7.91 | | Observation: severe fungus infestations also on other grape varieties | | | 10% | 10% | 5% | 2–3% | 0 | 0 | Severe infestation beginning |
| 5.7.91 | 3 | X | X | X | 10% | 10% | 5% | 0 | 0 | 0 | Fungus infestion stopped overnight |
| 9.7.91 | 4 | X | X | X | " | " | " | 0 | 0 | 0 | No further fungus infestation observed! |
| 18.7.91 | 5 | X | X | X | " | " | " | 0 | 0 | 0 | No further fungus infestation observed! |
| 30.7.91 | 6 | X | X | X | " | " | " | 0 | 0 | 0 | No further fungus infestation observed! |

TABLE 2

PLOT 2
VARIETY: SYLVANER
POSITION: SLOPE

| DATE | SPRAY No. | ROW | TREATMENT WITH Phos. | TREATMENT WITH Wagls. | TREATMENT WITH Lec. | INFESTATION WITH MILDEW LEAF | INFESTATION WITH MILDEW SHOOTS | INFESTATION WITH MILDEW GRAPE | INFESTATION WITH PERONOSPORA LEAF | INFESTATION WITH PERONOSPORA SHOOTS | INFESTATION WITH PERONOSPORA GRAPE | OBSERVATIONS |
|---|---|---|---|---|---|---|---|---|---|---|---|---|
| 13.6.91 | 1 | 1–4 + 8–10 | X | X | — | 1% | 1% | 0 | 0 | 0 | 0 | Light infestation |
|  |  | 5–7 | — | — | — | 1% | 1% | 0 | 0 | 0 | 0 | Light infestation (control) |
| 28.6.91 | 2 | 1–4 + 8–10 | X | X | — | 2% | 2% | 0 | 0 | 0 | 0 | Light infestation |
|  |  | 5–7 | — | — | — | 5% | 5% | 0 | 0 | 0 | 0 | Infestation has spread! |
| 2.7.91 |  | Observation: severe infestation by fungus |  |  |  |  |  |  |  |  |  |  |
|  |  | Increased in control rows 5–7: |  |  |  | 30% | 20% | 10% | 10% | 0 | 2% |  |
|  |  | Rows: 1–4 + 8–10 as plot 1: |  |  |  | 10% | 10% | 5% | 2–3% | 0 | 0 |  |
| 5.7.91 | 3 | 1–4 + 8–10 | X | X | — | 20% | 15% | 10% | 0 | 0 | 0 | Infestation with powdery mildew increased |
|  |  | 5–7 | — | — | — | 40% | 30% | 20% | 15% | 0 | 5% | Severe infestation (control) |
| 9.7.91 | 4 | 1–4 + 8–10 | X | X | — | 30% | 20% | 15% | 0 | 0 | 0 | Infestation with powdery mildew has spread |
|  |  | 5–7 | — | — | — | 50% | 30% | 40% | 20% | 0 | 10% | Infestation by peronospora stopped by climate conditions |
| 18.7.91 | 5 | 1–4 + 8–10 | X | X | 1 × 1 | 40% | 20% | 20% | 0 | 0 | 0 | Infestation by powdery mildew stopped |
|  |  | 5–7 | 1 × 1 | 1 × 1 | 1 × 1 | 60% | 40% | 60% | 20% | 0 | 10% | Fungus infestion stopped generally |
| 30.7.91 | 6 | 1–4 + 8–10 | X | X | X | 40% | 20% | 20% | 0 | 0 | 0 | No further infestation! |
|  |  | 5–7 | X | X | X | 60% | 40% | 60% | 20% | 0 | 10% | No further infestation! |

The examples of application of this spraying liquor onto the vineyard shown in FIG. 1 may be obtained from tables 1 and 2.

The values from tables 1 and 2 show that in comparison with no fungicide treatment by application of a spraying liquor with phosphite and waterglass (example II.2.), the infestation by powdery mildew (oidium) was reduced and the growth of peronospora after infestation by this fungus was prevented. With a severe fungus infestation by powdery mildew (oidium) this spraying liquor slowed down the infestation, but did not prevent it.

In addition to the already mentioned effects, the application of the composition in accordance with the invention (example II.3.) resulted in stopping the fungus infestation overnight even with severe infestation by powdery mildew (oidium). Also the fungus infestation by peronospora and the growth of this fungus was stopped overnight. Further, a comparison of tables 1 and 2 shows that through application of the composition in accordance with the invention in plot 1 on Jul. 5, 1991 (table 1, spraying no. 3), the developing severe infestation of fungus was completely stopped, whereas in plot 2 for the spraying liquor with phosphite and waterglass (table 2, spraying no. 3) the fungus infestation was not stopped. A synergistic effect of the composition in accordance with the invention lies additionally in the rapid stopping of the fungus infestation and in the acute effect against powdery mildew (oidium) in comparison with the components.

With respect to tables 1 and 2 it should be mentioned further that other winegrowers who preferred the conventional treatment, had to extend their treatment of the vineyards until the middle of August as a result of further fungus infestation through powdery mildew (oidium), peronospora and in addition botrytis. Further, no additional fungus diseases such as e.g. botrytis, red fire disease or black spot occurred in the previously mentioned test plots 1 and 2. The compositions in accordance with the invention should also be effective against the abovementioned fungus diseases. The use of the compositions against these fungus diseases represents a further embodiment of the invention.

With none of the spraying liquors used could a pollution of the environment with respect to human beings, animals, plants or micro organisms be observed.

We claim:

1. Fungicide composition comprising several active substances, whereby one active substance is a phosphite, characterized in that the composition includes a combination of active substances including at least one phosphite selected from the group consisting of $K_2HPO_3$, $KH_2PO_3$, $Na_2HPO_3$ and $NaH_2PO_3$, lecithin, and at least one compound selected from the group consisting of sodium metasilicate and soda waterglass, the phosphite being present in an amount from 0.05%–0.1% by weight, the lecithin in the mount from 0.04%–0.08% by weight and the sodium metasilicate and/or soda waterglass in an mount from 0.1–0.5% by weight respectively in relation to a watery composition.

2. Composition according to claim 1, characterized in that the phosphite is present in an amount from about 0.075% to about 0.08% by weight in relation to a watery composition.

3. Composition according to claims 1 or 2, characterized by an amount of lecithin of about 0.05% by weight, in relation to a watery composition.

4. Composition according to claim 1, characterized by an amount of soda waterglass and/or sodium metasilicate from about 0.2% to about 0.3% by weight in relation to a watery composition.

5. Composition according to claim 1, further comprising an amount of watery extracts and solutions from compost and/or worm humus and/or potassium hydrogen tartrate (tartar).

6. Method for treatment of fungus diseases in plants, in particular in vineyards and fruit orchards, or arable land and in vegetable gardens, hop cultivation and in ornamental plants, the method comprising: applying to plants a composition comprising several active substances, wherein the composition includes a combination active substances comprising:

at least one phosphite selected from the group consisting of $K_2HPO_3$, $KH_2PO_3$, $Na_2HPO_3$ and $NaH_2PO_3$, lecithin, and at least one compound selected from the group consisting of sodium metasilicate and soda waterglass.

7. Method according to claim 6, wherein said applying comprises prophylactically applying against fungus attack/infestation.

8. Method according to claim 6, wherein said applying comprises applying against acute fungus attack/infestation.

9. Method according to one of the previous claims 6 to 8, wherein said applying is carried out against peronospora.

10. Method according to one of the claims 6 to 8, wherein said applying is carried out against powdery mildew (oidium).

11. Method according to claim 6, wherein said applying comprises spraying.

12. Method according to claim 6, wherein said applying comprises wetting to dripping wetness.

* * * * *